United States Patent [19]

Terahara et al.

[11] 4,410,629
[45] Oct. 18, 1983

[54] ML-236B DERIVATIVES AND THEIR PREPARATION

[75] Inventors: Akira Terahara; Minoru Tanaka, both of Tokyo, Japan

[73] Assignee: Sankyo Company Limited, Tokyo, Japan

[21] Appl. No.: 351,974

[22] Filed: Feb. 24, 1982

Related U.S. Application Data

[62] Division of Ser. No. 270,846, Jun. 5, 1981, Pat. No. 4,346,227.

[30] Foreign Application Priority Data

Jun. 6, 1980 [JP] Japan ................... 55-76127
Aug. 22, 1980 [JP] Japan ................... 55-115483
Sep. 8, 1980 [JP] Japan ................... 55-124385
Sep. 19, 1980 [JP] Japan ................... 55-130311

[51] Int. Cl.³ .............................. C12P 7/42
[52] U.S. Cl. ...................... 435/146; 435/135; 435/136; 435/155; 435/886
[58] Field of Search ............... 435/135, 136, 146, 147, 435/148, 933, 939, 886, 155, 253–255; 560/119, 256

[56] References Cited

U.S. PATENT DOCUMENTS

| | | | |
|---|---|---|---|
| 3,983,140 | 9/1976 | Endo et al. | 435/933 X |
| 4,294,926 | 10/1981 | Monaghan et al. | 435/135 X |
| 4,319,039 | 3/1982 | Albers-Schonberg | 435/135 X |
| 4,342,767 | 8/1982 | Albers-Schonberg et al. | 435/135 X |

Primary Examiner—R. B. Penland
Attorney, Agent, or Firm—Frishauf, Holtz, Goodman & Woodward

[57] ABSTRACT

Compounds of formula (I):

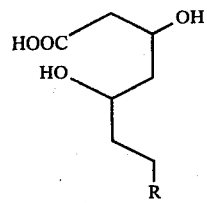

(wherein R represents a group of formula

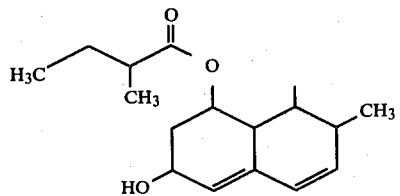

or

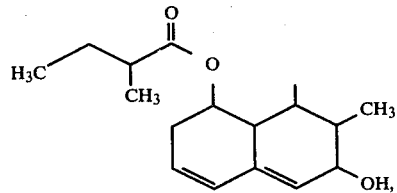

and the corresponding ring-closed lactones, salts (especially alkali metal salts) and esters (especially $C_1$–$C_5$ alkyl esters) thereof may be prepared by subjecting ML-236B, or ML-236B carboxylic acid or a salt or ester thereof to enzymatic hydroxylation, which may be effected by means of microorganisms of the genera Mucor, Rhizopus, Zygorynchus, Circinella, Actinomucor, Gongornella, Phycomyces, Martierella, Pycnoporus, Rhizoctonia, Absidia, Cunninghamella, Syncephalastrum and Streptomyces, or cell-free, enzyme-containing extracts from said microorganisms. The compounds are capable of inhibiting biosynthesis of cholesterol and are thus useful in the treatment of hypercholesteraemia.

24 Claims, 5 Drawing Figures

ML-236B DERIVATIVES AND THEIR PREPARATION

This is a division of application Ser. No. 270,846 filed June 5, 1981, which issued as U.S. Pat. No. 4,346,227.

BACKGROUND TO THE INVENTION

The present invention relates to a series of new derivatives of the known compound ML-236B, to processes for their preparation and to pharmaceutical compositions containing them.

ML-236B, which has the following chemical structure:

is disclosed in U.S. Pat. No. 3,983,140. It has been isolated and purified from the metabolic products of microorganisms of the genus Penicillium, especially *Penicillium citrinum*, a species of blue mould. It has been shown to inhibit the biosynthesis of cholesterol by enzymes or cultured cells separated from experimental animals by competing with the rate-limiting enzyme active in the biosynthesis of cholesterol, namely 3-hydroxy-3-methylglutaryl-coenzyme A reductase and, as a result, significantly reduces serum cholesterol levels of animals [Journal of Antibiotics, 29, 1346 (1976)]. A number of compounds structurally related to ML-236B have also been discovered and found to possess the ability to inhibit the biosynthesis of cholesterol.

We have now discovered a series of new compounds, which may be prepared by the enzymatic hydroxylation of ML-236B or of derivatives thereof, and which possess an ability to inhibit the biosynthesis of cholesterol which is at least comparable with, and in some instances substantially exceeds, that of ML-236B itself.

BRIEF SUMMARY OF INVENTION

The compounds of the present invention are those hydroxycarboxylic acids of formula (I):

(in which R represents a group of formula or and ring-closed lactones, salts and esters thereof.

The invention also provides a process for preparing a compound of formula (I), or a ring-closed lactone, salt or ester thereof by the enzymatic hydroxylation of ML-236B, or ML-236B carboxylic acid, or a salt or ester thereof.

ML-236B carboxylic acid has the formula

DETAILED DESCRIPTION OF INVENTION

One class of compounds of the present invention are those compounds of formula (II):

(in which $R^1$ represents a hydrogen atom or a $C_1$–$C_5$ alkyl group), pharmaceutically acceptable salts of the acid wherein $R^1$ represents a hydrogen atom, and the corresponding lactone of formula (III):

(III)

In view of the number of asymmetric carbon atoms in these compounds, a variety of geometric isomers are possible. Of these, the most important isomers are as follows:

Compounds of formula (IV):

(IV)

(in which $R^1$ is as defined above) and pharmaceutically acceptable salts of the acid wherein $R^1$ represents a hydrogen atom, and the corresponding lactone of formula (V):

(V)

and compounds of formula (VI):

(VI)

(in which $R^1$ is as defined above), and pharamceutically acceptable salts of the acid wherein $R^1$ represents a hydrogen atom and the corresponding lactone of formula (VII):

(VII)

The hydroxy-carboxylic acid of formula (IV) in which $R^1$ represents a hydrogen atom is herein referred to as M-4 and derivatives of this acid, specifically the salts and esters, are named as derivatives of M-4, whilst the corresponding lactone of formula (V) is herein referred to as M-4 lactone. Similarly, the hydroxy-carboxylic acid of formula (VI) in which $R^1$ represents a hydrogen atom is referred to as M-4' and derivatives of this acid are referred to as derivatives of M-4', whilst the corresponding lactone of formula (VII) is referred to as M-4' lactone.

Another preferred class of compounds of the invention are those compounds of formula (VIII):

(VIII)

(in which $R^1$ is as defined above), and pharmaceutically acceptable salts of the acid in which $R^1$ represents a hydrogen atom, and the corresponding lactone of formula (IX):

(IX)

A variety of geometric isomers of these compounds are also possible, the most important being the following:

Compounds of formula (X):

(X)

(in which R¹ is as defined above), and pharmaceutically acceptable salts of the acid in which R¹ represents a hydrogen atom and the corresponding lactone of formula (XI):

(XI)

and compounds of formula (XII):

(XII)

(in which R¹ is as defined above), and pharamceutically acceptable salts of the acid in which R¹ represents a hydrogen atom and the corresponding lactone of formula (XIII):

(XIII)

The acid of formula (X) is herein referred to as IsoM-4 and its derivatives, such as salts and esters, are named as derivatives of IsoM-4, whilst the corresponding lactone of formula (XI) is herein referred to as IsoM-4 lactone. The acid of formula (XII) in which R¹ represents a hydrogen atom is herein referred to IsoM-4', and its derivatives are named as derivatives of IsoM-4', whilst its corresponding lactone of formula (XIII) is herein referred to as IsoM-4' lactone.

Of the esters of the hydroxy-carboxylic acids of formula (I), the $C_1$–$C_5$ alkyl esters are preferred. These alkyl groups may be straight or branched-chain groups and include, for example the methyl, ethyl, propyl, isopropyl, butyl and isobutyl groups, of which the methyl group is particularly preferred.

The hydroxy-carboxylic acids will also form salts with a variety of cations, particularly metals and most preferably alkali metals, such as sodium or potassium. The sodium salts are most preferred.

Of the compounds of the invention, the most preferred compounds are M-4 lactone, M-4 sodium salt, M-4 methyl ester, IsoM-4' lactone, IsoM-4' sodium salt and IsoM-4' methyl ester, M-4 sodium salt being particularly preferred.

The compounds of the invention may be prepared by the enzymatic hydroxylation of ML-236B or of a derivative thereof, specifically ML-236B carboxylic acid or a salt or ester thereof.

This enzymatic hydroxylation may be effected as part of the mammalian metabolism of ML-236B or a derivative thereof, for example by administering ML-236B to a suitable animal, collecting a metabolic product, eg. urine, and then separating the desired compound or compounds of the invention from the urine. Alternatively, the liver or an enzyme-containing extract from the liver may be used instead of the living animal. However, processes employing the animal metabolism or animal products have a relatively low productivity and are difficult to effect reproducibly. Accordingly, we prefer to employ microorganisms or enzyme-containing extracts from the microorganisms.

Accordingly, the process of the present invention is preferably effected using a microorganism capable of converting ML-236B or a derivative thereof to a compound of the present invention or using an enzyme-containing extract of such a microorganism. Particularly preferred microorganisms are those of the following genera: Mucro, Rhizopus, Zygorynchus, Circinella, Actinomucor, Gongronella, Phycomyces, Martierella, Pycnoporus, Rhizoctonia, Absidia, Cunninghamela, Syncephalasporum and Streptomyces. In particular the following species are preferred:

Absidia coerulea
Cunninghamella echinulata
Syncephal strum racemosum
Streptomyces roseochromogenus
Mucor hiemalis, f. hiemalis
Mucor bacilliformis
Mucor circinelloides f. circinelloides
Mucor hiemalis f. corticolus
Mucor dimorphosphorus
Mucor fragilis
Mucor genevensis
Mucor globosus
Mucor circinelloides f. griseo-cyanus
Mucor heterosporus
Mucor spinescens
Rhizopus chinensis
Rhizopus circinans
Rhizopus arrhizus
Zygorynchus moelleri
Circinella muscae

*Circinella rigida*
*Circinella umbellata*
*Actinomucor elegans*
*Phycomyces blakesleeanus*
*Martierella isbellina*
*Gongronella butleri*
*Pycnopdrus coccineus*
*Rhizoctonia solani*
*Syncephalastrum nigricans*
*Absidia glauca* var. *paradoxa*

Amongst strains of the above species, the following are particularly preferred:
*Absidia coerulea* IFO-4423
*Cunninghamella echinulata* IFO-4445
*Cunninghamella echinulata* IFO-4444
*Cunninghamella echinulata* ATCC-9244
*Syncephalastrum racemosum* IFO-4814
*Syncephalastrum racemosum* IFO-4828
*Streptomyces roseochromogenus* NRRL-1233
*Streptomyces roseochromogenus* IFO-3363
*Streptomyces roseochromogenus* IFO-3411
*Mucor hiemalis f. hiemalis* IFO-5834
*Mucor hiemalis f. hiemalis* IFO-5303
*Mucor hiemalis f. hiemalis* IFO-8567
*Mucor hiemalis f. hiemalis* IFO-8449
*Mucor hiemalis f. hiemalis* IFO-8448
*Mucor hiemalis f. hiemalis* IFO-8565
*Mucor hiemalis f. hiemalis* CBS-117.08
*Mucor hiemalis f. hiemalis* CBS-109.19
*Mucor hiemalis f. hiemalis* CBS-200.28
*Mucor hiemalis f. hiemalis* CBS-242.35
*Mucor hiemalis f. hiemalis* CBS-110.19
*Mucor hiemalis f. hiemalis* CBS-201.65
*Mucor bacilliformis* NRRL-2346
*Mucor circinelloides f. circinelloides* IFO-4554
*Mucor circinelloides f. circinelloides* IFO-5775
*Mucor hiemalis f. corticolus* NRRL-12473
*Mucor dimorphosphorus* IFO-4556
*Mucor fragilis* CBS-236.35
*Mucor genevensis* IFO-4585
*Mucor globosus* NRRL 12474
*Mucor circinelloides f. griseo-cyanus* IFO-4563
*Mucor heterosporus* NRRL-3154
*Mucor spinescens* IAM-6071
*Rhizopus chinesis* IFO-4772
*Rhizopus circinans* ATCC-1225
*Rhizopus arrhizus* ATCC-11145
*Zygorynchus moelleri* IFO-4833
*Circinella muscae* IFO-4457
*Circinella rigida* NRRL-2341
*Circinella umbellata* NRRL-1713
*Circinella umbellata* IFO-4452
*Circinella umbellata* IFO-5842
*Phycomyces blakesleeanus* NRRL-12475
*Martierella isabellina* IFO-6739
*Gongronella butleri* IFO-8080
*Pycnoporus coccineus* NRRL-12476
*Rhizoctonia solani* NRRL-12477
*Syncephalastrum nigricans* NRRL-12478
*Syncephalastrum nigricans* NRRL-12479
*Syncephalastrum nigricans* NRRL-12480
*Absidia glauca* var. *paradoxa* IFO-4431
*Actinomucor elegans* ATCC-6476

The microorganisms listed above are available from International Culture Collections, as indicated by the codes appended to their accession numbers, which codes have the following meanings.

IFO = Institute for Fermentation, Osaka, Japan
NRRL = Novthern Utilization Research and Development Division, U.S. Department of Agriculture, Peoria, Ill. U.S.A.
CBS = Centraal bureau voor Schimmelcultures, Netherlands
IAM = Institute of Applied Microbiology, Tokyo, Japan
ATCC = American Type Culture Collection, Maryland, U.S.A.

Of the species noted above, the following are particularly preferred:
*Absidia coerulea*
*Cunninghamella echinulata*
*Syncephalastrum racemosum*
*Mucor hiemalis f. hiemalis*
*Mucor bacilliformis*
*Mucor circinalloides f. circinelloides*
*Mucor hiemalis f. corticolus*
*Mucor dimorphosporus*
*Mucor fragilis*
*Mucor genevensis*
*Mucor globosus*
*Mucor circinelloides f. griseo-cyanus*
*Mucor heterosporus*
*Mucor spinescens*
*Pycnoporus coccineus*
*Rhizoctonia solani*
*Syncephalastrum nigricans* and the following are particularly preferred strains of the species:
*Absidia coerulea* IFO-4423
*Cunninghamella echinulata* IFO-4445
*Cunninghamella echinulata* IFO-4444
*Cunninghamella echinulata* ATCC-9244
*Syncephalastrum racemosum* IFO-4814
*Syncephalastrum racemosum* IFO-4828
*Mucor hiemalis f. hiemalis* IFO-5834
*Mucor hiemalis f. hiemalis* IFO-5303
*Mucor hiemalis f. hiemalis* IFO-8567
*Mucor hiemalis f. hiemalis* IFO-8449
*Mucor hiemalis f. hiemalis* IFO-8448
*Mucor hiemalis f. hiemalis* IFO-8565
*Mucor hiemalis f. hiemalis* CBS-117.08
*Mucor hiemalis f. hiemalis* CBS-109.19
*Mucor hiemalis f. hiemalis* CBS-200.28
*Mucor hiemalis f. hiemalis* CBS-242.35
*Mucor hiemalis f. hiemalis* CBS-110.19
*Mucor hiemalis f. hiemalis* CBS-201.65
*Mucor bacilliformis* MRRL-2346
*Mucor circinelloides f. circinelloides* IFO-4554
*Mucor circinelloides f. circinelloides* IFO-5775
*Mucor hiemalis f. corticolus* NRRL-12473
*Mucor dimorphosphorus* IFO-4556
*Mucor fragilis* CBS-236.35
*Mucor genevensis* IFO-4585
*Mucor globosus* NRRL 12474
*Mucor circinelloides f. griseo-cyanus* IFO-4563
*Mucor heterosporus* NRRL-3154
*Mucor spinescens* IAM-6071
*Pycnoporus coccineus* NRRL-12476
*Rhizoctonia solani* NRRL-12477
*Syncephalastrum nigricans* NRRL-12478
*Syncephalastrum nigricans* NRRL-12479
*Syncephalastrum nigricans* NRRL-12480

For the preparation of compounds of formulae (IV) and (V) and their salts, the following species are preferred:
*Mucor hiemalis f. hiemali*

*Mucor circinelloides f. circinelloides*
*Mucor fragilis*
*Mucor genevensis*
*Mucor circinelloides f. griseo-cyanus*
*Pycnoporus coccineus*
*Rhizoctonia solani.*

For the preparation of compounds of formula (VI) and (VIII) and their salts, the species *Syncephalastrum nigricans* and *Syncephalastrum racemosum* are preferred.

For the preparation of compounds of formula (VIII) and (IX) and their salts, the species *Absidia coerulea* and *Cunninghamella echinulata* are preferred.

Of all of the species listed above, *Mucor hiemalis f. hiemalis* is particularly preferred since it is able to convert ML-236B and its derivatives to the desired compounds of formula (I) at a conversion of 90% or even higher.

Conversion of ML-236B or derivatives thereof to compounds of formula (I) may be achieved by contacting the complete cellular microorganism or, in some cases, a cell-free extract from the microorganism with ML-236B or a derivative thereof. The form of the compound produced will depend upon the culture conditions and the form of microorganism employed. Thus, for example, if the complete cellular microorganism is cultivated in the presence of ML-236B or a derivative thereof, the product will be the carboxylic acid, the lactone or alkali metal salt, depending upon the culture conditions, particularly the pH. On the other hand, if the ML-236B or derivative thereof is simply contacted with a resting cellular system or with a cell-free extract, the compound of the invention is obtained in the form of an alkali metal salt.

The progress of the conversion reaction may be determined by assaying samples of the reaction mixture during the course of the reaction to determine the degree of conversion. For example, the presence of M-4 lactone may be assayed by liquid chromatography employing as a carrier $\mu$ Bondapak $C_{18}$ (manufactured by Waters Co. U.S.A.) and as the solvent 62% v/v aqueous methanol at the rate of 1 ml/minute. When detected using its ultraviolet absorption at 237 nm, M-4 gives a peak at a retention time of 10 minutes, and this may be used for the assay. Similar techniques are available for assaying the other compounds of the invention.

Where the microorganisms are to be cultivated in the presence of ML-236B or a derivative thereof to product the compounds of the invention, the culture conditions and culture media employed will be chosen having regard to the particular micoorganism to be cultivated. Since the species of micoorganism proposed for use in the process of the present invention are well known, culture conditions and culture media for use with these microorganisms are also well known.

The compounds of the invention may be separated from the reaction mixture by conventional means, for example by filtering off microbial cells (if necessary) and then subjecting the remaining mixture to any combination of thin layer chromatography, column chromatography or high performance liquid chromatography. The various compounds of the invention, where two or more are prepared together, may be separated from each other in the course of one or more of these chromatographic purification steps.

In addition to the compounds of the invention, there may, in some cases, also be prepared a compound which we have designated M-3 and which is known under the name 3',5'-dihydroxy(dihydro-ML-236B) in a copending application entitled "Hydronaphthalene Derivatives, their Preparation and Use". This may also be separated in the same way.

We have found that the compounds of the invention give a 50% inhibition of cholesterol biosynthesis at concentrations comparable with, or, in some cases, significantly less than, the concentrations required by ML-236B and certain other similar known compounds. The inhibitory activities of the compounds of the invention, in terms of the concentration in $\mu$g/ml required to inhibit cholesterol biosynthesis by 50% [measured by the method described in the Journal of Biological Chemistry, 234, 2835 (1959)] are as follows:

| | |
|---|---|
| M-4 methyl ester | 0.001 |
| M-4 sodium salt | 0.0008 |
| M-4 lactone | 0.016 |
| IsoM-4' methyl ester | 0.007 |
| IsoM-4' lactone | 0.013 |
| M-4' lactone | 0.019 |
| M-4' sodium salt | 0.00049 |
| ML-236B | 0.01 |

The invention is further illustrated by the following Examples.

EXAMPLE 1

Preparation of M-4 lactone

Twenty 500 ml Sakaguchi flasks, each containing 100 ml of a medium having the composition described below, were inoculated with spores of *Absidia coerulea* IFO 4423. The flasks were subjected to shaking culture at 26° C. and 120 Strokes/min (s.p.m.) for 2 days. At the end of this time, the sodium salt of ML-236B was added to each of the flasks to a final concentration of 0.05% w/v. Cultivation was continued at 26° C. and 120 s.p.m. for a further 5 days.

The composition of the medium was (percentages are w/v):

| | |
|---|---|
| Glucose | 2.0% |
| $K_2HPO_4$ | 0.15% |
| $MgSO_4.7H_2O$ | 0.15% |
| $NH_4NO_3$ | 0.1% |
| Peptone | 0.1% |
| Corn steep liquor | 0.2% |
| Yeast extract | 0.1% |
| $ZnSO_4.7H_2O$ | 0.001% |
| Tap water | the balance (adjusted to pH 7.0). |

After completion of the cultivation, the reaction liquor was filtered, and the filtrate was adjusted with trifluoroacetic acid to pH 3. The resulting mixture was extracted with three 1 liter portions of ethyl acetate, to give extracts containing M-4. This compound shows an Rf value of 0.45 on thin layer chromatography (TLC) (Plate: Merck silica gel Art 5715; solvent: a 50:50:3 by volume mixture of benzene, acetone and acetic acid). The combined extracts were washed with saturated aqueous sodium chloride, and then a catalytic amount of trifluoroacetic acid was added for lactonization. The resulting mixture was then washed with a 1% w/v aqueous solution of sodium bicarbonate, dried over anhydrous sodium sulphate and evaporated under reduced pressure to dryness. The residue was subjected to preparative liquid chromatography, System 500 using a Prep PAK-500/$C_{18}$ cartridge manufactured by Waters Associates (Prep PAK is a Trade Mark). Purification with a 55% v/v aqueous methanol system yielded 50.1 mg of M-4 lactone.

Figure 1:
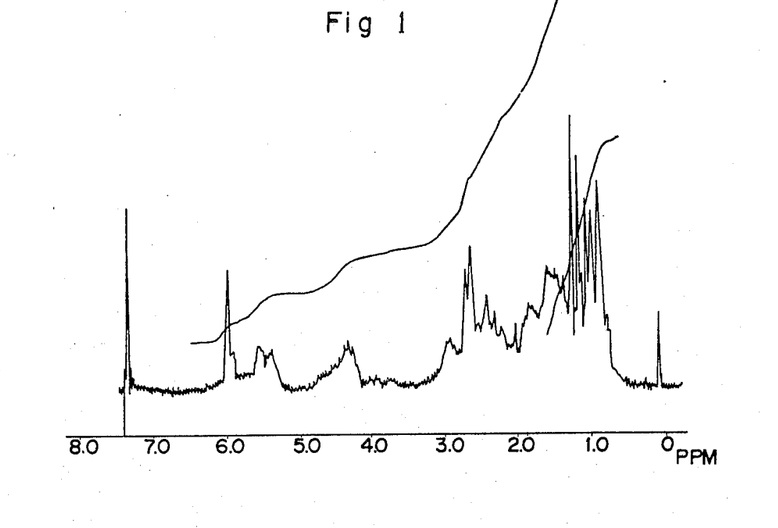

M-4 lactone has the following physical properties.
(1) Nuclear Magnetic Resonance Spectrum:
The NMR spectrum measured at 60 MHz in deuterochloroform using tetramethylsilane as the internal standard is shown in FIG. 1 of the accompanying drawings.
(2) Ultraviolet absorption spectrum (methanol solution) $\lambda_{max}$nm: 230; 236.7; 244.6.
(3) Infrared absorption spectrum (liquid film) $\nu cm^{-1}$: 3400, 2950, 1725.
(4) Thin layer chromatography:
TLC plate: Merck silica gel Art 5715;
Solvent: benzene, acetone, acetic acid (50:50:3 by volume);
Rf value: 0.62.

EXAMPLE 2

48 mg of M-4 lactone were prepared following the same procedures as in Example 1, but using *Cunninghamella echinulata* IFO 4445.

EXAMPLE 3

30 mg of M-4 lactone were prepared following the same procedures as in Example 1, but using *Streptomyces roseochromogenus* NRRL 1233.

EXAMPLE 4

5 mg of M-4 lactone were prepared following the same procedures as in Example 1, but using *Syncephalastrum racemosum* IFO 4814.

EXAMPLE 5

6 mg of M-4 lactone were prepared following the same procedures as in Example 1, but using *Syncephalastrum racemosum* IFO 4828.

EXAMPLE 6

Preparation of IsoM-4'methyl ester

Twenty 500 ml Sakaguchi flasks, each containing 100 ml of a medium having the composition described below, were inoculated with spores of *Absidia coerulea* IFO 4423. The flasks were subjected to shaking culture at 120 s.p.m. and 26° C. for 2 days. At the end of this time, the sodium salt of ML-236B was added to each of the flasks to a final concentration of 0.05% w/v. Cultivation was continued at 120 s.p.m. and 26° C. for a further 5 days.

The composition of the medium was (percentages are w/v):

| | |
|---|---|
| Glucose | 2.0% |
| K$_2$HPO$_4$ | 0.15% |
| MgSO$_4$.7H$_2$O | 0.15% |
| NH$_4$NO$_3$ | 0.1% |
| Peptone | 0.1% |
| Corn steep liquor | 0.2% |
| Yeast extract | 0.1% |
| ZnSO$_4$.7H$_2$O | 0.001% |
| Tap water | the balance (adjusted to pH 7.0). |

Figure 2:
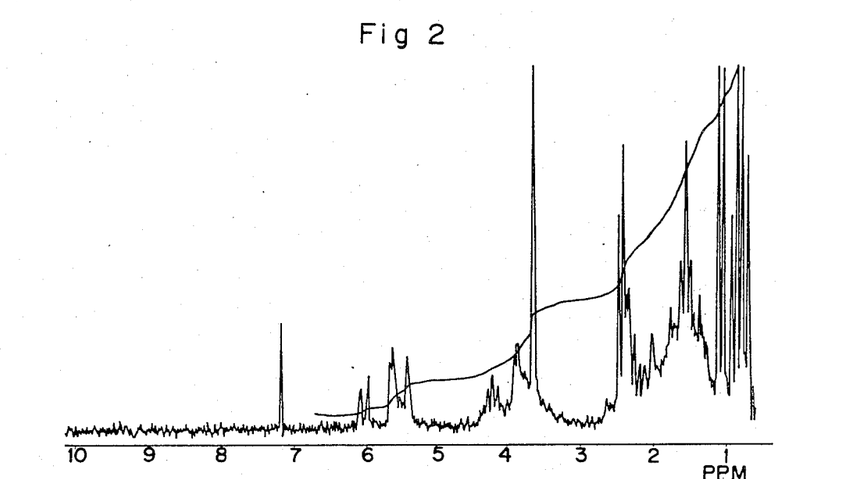
Figure 3:
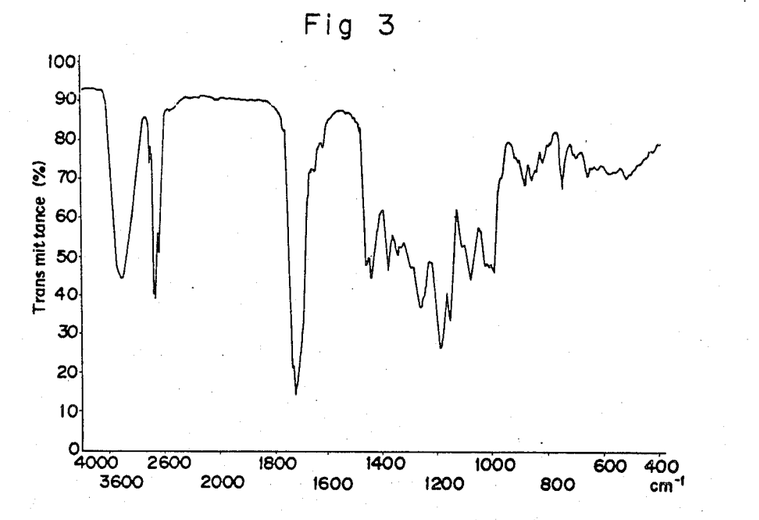

After completion of the cultivation, the reaction liquor was filtered, and the filtrate was adjusted with trifluoroacetic acid to pH 3. The resulting mixture was extracted with three 1 liter portions of ethyl acetate to give extracts containing IsoM-4'. This compound has an Rf value of 0.45 on thin layer chromatography (plate: Merck silica gel Art 5715; solvent: a 50:50:3 by volume mixture of benzene, acetone and acetic acid). The extract was washed with a saturated aqueous solution of sodium chloride, and then an ethereal solution of diazomethane was added. The mixture was allowed to stand for 30 minutes and then evaporated under reduced pressure to dryness. The residue was placed on a Lobar column (Merck Si 60, Size A) and purified using as the solvent system a 1:1 by volume mixture of benzene and ethyl acetate. There were obtained 200 mg of an IsoM-4'methyl ester fraction. This fraction was further purified on a Lobar column (Merck RP-8, Size A) using 35% v/v aqueous acetonitrile as the eluent to give 78 mg of pure IsoM-4'methyl ester, having the following characteristics:

(1) Nuclear Magnetic Resonance Spectrum:
The NMR spectrum measured at 100 MHz in deuterochloroform using tetramethylsilane as the internal standard is shown in FIG. 2 of the accompanying drawings.
(2) Mass spectrum:
Measurement was made [after silylation with N,O-bis(trimethylsilyl)trifluoroacetamide] using a mass spectrometer, type D-300 manufactured by Nippon Electronics.
M/e: 654 (M+), 552, 462, 372, 272, 233, 231.
(3) Ultraviolet absorption spectrum (methanol solution) $\lambda_{max}$nm: 229; 234.8; 244.5.
(4) Infrared absorption spectrum (liquid film):
As shown in FIG. 3 of the accompanying drawings.
(5) Thin layer chromatography:
TLC plate: Merck silica gel Art 5715;
Solvent: benzene, acetone (1:1 by volume);
Rf value: 0.88.

By operating as described above but replacing the diazomethane by another appropriate diazoalkane, it is possible to produce other esters of IsoM-4'.

EXAMPLE 7

Preparation of IsoM-4'lactone

Figure 4:
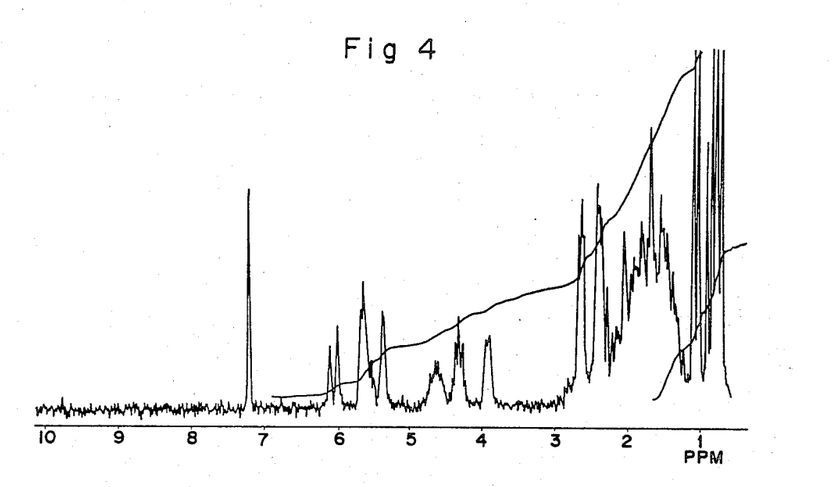
Figure 5:
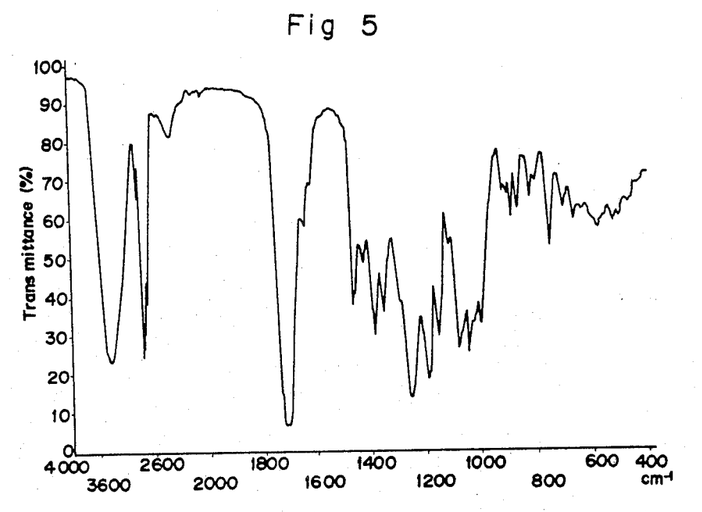

The procedure described in Example 6 was repeated up to and including extraction with ethyl acetate to give extracts containing IsoM-4'. The combined extracts were washed with a saturated aqueous solution of sodium chloride and then evaporated to dryness to give the lactone product. The resulting residue was placed on a Lobar column (Merck Si 60, Size A) and purified using as the solvent system a 1:1 by volume mixture of benzene and ethyl acetate, to afford 198 mg of IsoM-4'lactone. This product was further purified by means of a Lobar column (Merck RP-8, Size A) eluted with 35% v/v aqueous acetonitrile, to give 82 mg of pure IsoM-4 lactone, having the following characteristics:

(1) Nuclear Magnetic Resonance Spectrum:
The NMR spectrum measured at 100 MHz in deuterochloroform using tetramethylsilane as the internal standard is shown in FIG. 4 of the accompanying drawings.
(2) Ultraviolet absorption spectrum (methanol solution) $\lambda_{max}$nm: 229; 234.8; 244.5.
(3) Infrared absorption spectrum (liquid film):
As shown in FIG. 5 of the accompanying drawings.

EXAMPLE 8

63 mg of IsoM-4'lactone were prepared, following the same procedures as in Example 7, but using *Cunninghamella echinulata* IFO 4445.

EXAMPLE 9

24 mg of IsoM-4'lactone were prepared, following the same procedures as in Example 7, but using *Syncephalastrum racemosum* IFO 4814.

EXAMPLE 10

35 mg of IsoM-4'lactone were prepared, following the same procedures as in Example 7, but using *Syncephalastrum racemosum* IFO 4828.

EXAMPLE 11

12 mg of IsoM-4'lactone were produced according to the process described in Example 7, but using *Streptomyces roseochromogenus* NRRL 1233.

EXAMPLE 12

Preparation of IsoM-4'sodium salt

In a small amount of acetone were dissolved 10 mg of IsoM-4'lactone. To the solution was added an equivalent amount of sodium hydroxide and the mixture was allowed to stand for 1 hour. The pH of the resulting mixture was adjusted with 0.1 N hydrochloric acid to a value of 8.0. The acetone was then distilled off, and the residue was placed on an XAD-20 column (about 20 ml). The column was washed with distilled water and then eluted with 50 ml of 50% v/v aqueous acetone. The acetone was again distilled off, and the residue was freeze-dried to afford 6 mg of IsoM-4'sodium salt, having the following characteristics:

(1) Ultraviolet absorption spectrum (methanol solution) $\lambda_{max}$nm: 229 (shoulder); 235; 245 (shoulder).

(2) Infrared absorption spectrum (KBr) $\nu$cm$^{-1}$: 3400, 2850, 1710, 1580.

(3) Thin layer chromatography:
  TLC plate: Merck silica gel Art 5715;
  Solvent: benzene, acetone, acetic acid (50:50:3 by volume);
  Rf value: 0.45.

EXAMPLE 13

Preparation of M-4 methyl ester

Twenty 500 ml Sakaguchi flasks, each containing 100 ml of a medium of the same composition as shown in Example 1, were inoculated with spores of *Absidia coerulea* IFO 4423. The flasks were subjected to shaking culture at 26° C. and 120 s.p.m. for 2 days. The sodium salt of ML-236B was then added to each of the flasks to a final concentration of 0.05% w/v. Cultivation was continued at 26° C. and 120 s.p.m. for a further 5 days. After completion of the cultivation, the reaction liquor was filtered, and the filtrate was adjusted with trifluoroacetic acid to pH 3. The resulting mixture was extracted with three 1 liter portions of ethyl acetate, to give extracts containing M-3, M-4 and IsoM-4'. Both M-4 and IsoM-4' show an Rf value of 0.45 on thin layer chromatography (Plate: Merck silica gel Art 5715; solvent: a 50:50:3 by volume mixture of benzene, acetone and acetic acid). The combined extracts were washed with saturated aqueous sodium chloride, and then an ethereal solution of diazomethane was added. The mixture was allowed to stand for 30 minutes and then evaporated under reduced pressure to dryness. When the residue was placed on a Lobar column (Merck Si 60, Size A), and purification was effected using a 1:1 by volume mixture of benzene and ethyl acetate, a fraction containing IsoM-4'methyl ester and a fraction containing M-4 methyl ester were separated. There were obtained 185.3 mg of the latter active fraction, from which 20 mg of pure M-4 methyl ester were obtained as a colourless oil by using a Lobar column (Merck RP-8, Size A) and eluting with 35% v/v aqueous acetonitrile.

M-4 methyl ester has the following characteristics:

(1) Nuclear Magnetic Resonance Spectrum:
Measurement was made at 200 MHz in deuterochloroform using tetramethylsilane as the internal standard.

$\delta$ppm:
  0.88 (3H, triplet, J=7.3 Hz);
  0.89 (3H, doublet, J=6.5 Hz);
  1.12 (3H, doublet, J=6.8 Hz);
  1.1–1.7 (10H, multiplet);
  2.34 (1H, sextuplet, J=7 Hz);
  2.3–2.5 (2H, multiplet);
  2.49 (2H, doublet, J=6.4 Hz);
  2.58 (1H, multiplet);
  3.72 (3H, singlet);
  3.78 (1H, multiplet);
  4.25 (1H, quintet, J=7 Hz);
  4.4 (1H, multiplet);
  5.42 (1H, multiplet);
  5.56 (1H, multiplet);
  5.90 (1H, doubled doublet, J=9.8 and 5.6 Hz);
  5.99 (1H, doublet, J=9.8 Hz).

(2) Mass spectrum:
Measurement was made [after silylation with N,O-bis(trimethylsilyl)trifluoroacetamide] using a mass spectrometer, type D-300 manufactured by Nippon Electronics.
M/e: 654 (M+), 552, 462, 372, 290, 272, 233, 231.

(3) Ultraviolet absorption spectrum (ethanol solution) $\lambda_{max}$nm: 230.1; 237.3; 246.4.

(4) Infrared absorption (liquid film) $\nu$cm$^{-1}$: 3400, 2950, 1730.

(5) Thin layer chromatography:
  TLC plate: Merck silica gel Art 5715;
  Solvent: benzene and acetone (1:1 by volume):
  Rf value: 0.88.

By operating as described above but replacing the diazomethane by another appropriate diazoalkane, it is possible to produce other esters of M-4.

EXAMPLE 14

Preparation of Sodium Salts of M-4 and IsoM-4'

The procedure described in Example 1 except that Na'$_2$HPO$_4$ was used instead of the K$_2$HPO$_4$ was repeated up to and including filtration of the reaction liquor. The filtrate was then adsorbed on an HP-20 column (manufactured by Mitsubishi Chemical Industries). After washing the column with water, fractions containing M-4 sodium salt, IsoM-4' sodium salt and M-3 sodium salt were eluted with 50% v/v aqueous acetone. The active fractions were freeze-dried, giving 830 mg of a freeze-dried product, which was purified by repeatedly subjecting it to high-performance liquid chromatography (column: $\mu$ Bondapak C$_{18}$, 40% v/v aqueous methanol 1 ml/min.) to give 32 mg of M-4 sodium salt and 280 mg of IsoM-4' sodium salt.

The properties of the IsoM-4' sodium salt were identical to those of the product of Example 12 and the properties of the M-4 sodium salt are as follows:

(1) Nuclear Magnetic Resonance Spectrum:

Measurement was made at 200 MHz in deuteromethanol using tetramethylsilane as the internal standard.

δ ppm:
0.91 (3H, triplet, J=7.5 Hz);
0.92 (3H, doublet J=7 Hz);
1.12 (3H, doublet, J=7 Hz);
1.1–1.8 (10H, multiplet);
2.25 (1H, doubled doublet, J=15 and 7.6 Hz);
2.34 (1H, doubled doublet, J=15 and 5.5 Hz);
2.2–2.4 (3H, multiplet);
2.48 (1H, multiplet);
3.68 (1H, multiplet);
4.07 (1H, multiplet);
4.28 (1H, multiplet);
5.36 (1H, multiplet);
5.48 (1H, doubled doublet, J=3 and 2 Hz);
5.88 (1H, doubled doublet, J=9.6 and 5.3 Hz);
5.98 (1H, doublet, J=9.8 Hz).

(2) Ultraviolet absorption spectrum (methanol solution) $\lambda_{max}$nm: 230.0; 237.2; 245.0.

(3) Infrared absorption spectrum (KBr) $\nu cm^{-1}$; 3400, 2900, 1725, 1580.

(4) Thin layer chromatography:
TLC plate: Merck silica gel Art 5715;
Solvent: benzene, acetone and acetic acid (50:50:3 by volume);
Rf value: 0.45.

EXAMPLE 15

18 mg of M-4 methyl ester were prepared, following the same procedures as in Example 13, but using *Cumminghamella echinulata* IFO 4445.

EXAMPLE 16

33 mg of M-4 methyl ester were prepared, following the same procedures as in Example 13, but using *Streptomyces roseochromogenus* NRRL 1233.

EXAMPLE 17

12 mg of M-4 methyl ester were prepared, following the same procedures as in Example 13, but using *Syncephalastrum racemosum* IFO 4814.

EXAMPLE 18

16 mg of M-4 methyl ester were prepared, following the same procedures as in Example 13, but using *Syncephalastrum racemosum* IFO 4828.

EXAMPLE 19

Preparation of M-4 methyl ester

Five beagles (male, average weight 10 kg) were administered with ML-236B at a dose of 200 mg/kg/day and their urine was collected for 3 days. 3 liters of collected urine were passed through a 500 ml XAD-2 column, eluted with 500 ml of 50% v/v aqueous acetone, and, after distilling off the acetone under reduced pressure, the residual liquid was adjusted to pH 3 by the addition of trifluoroacetic acid. The mixture was then extracted three times, each time with 1 liter of ethyl acetate to give M-4. This compound shows an Rf value of 0.45 on thin layer chromatography (TLC plate: Silica Gel Art 5715 manufactured by Merck & Co., Inc.; solvent: a 50:50:3 by volume mixture of benzene, acetone and acetic acid). The extract was washed with a saturated aqueous solution of sodium chloride, and, after adding an ethereal solution of diazomethane, left standing for 30 minutes. It was then evaporated to dryness under reduced pressure. The residue was dissolved in 10 ml of a 55% v/v aqueous methanol solution, and passed through a column chromatograph (Product of Merck & Co., Inc.; RP-8, Size B). After passing 200 ml of a 55% v/v aqueous methanol solution, it was eluted with a 60% v/v aqueous methanol solution. The first 240 ml of the eluate were discarded, and the next 120 ml were collected. This fraction was evporated to dryness and the residue was dissolved in 2.5 ml of a 65% v/v aqueous methanol solution and purified by high-performance liquid chromatography (JASCO-Trirotar, column: μ-Bondapak $C_{18}$). The portion which showed the fourth peak was separated and the solvent was distilled off to give M-4 methyl ester as a colourless oil having the properties shown in Example 13. 4 mg of product were obtained.

EXAMPLE 20

Preparation of M-4

Homogenized rabbit liver was used in this Example to obtain M-4 from ML-236B.

(a) Enzymatic solution

Three volumes of a 1.15% w/v potassium chloride-10 mM phosphate (pH 7.4) buffer solution were added to one volume of rabbit liver and the mixture was homogenized. The homogenized mixture was then centrifuged for 20 minutes at 9.000 xg, and the supernatant fraction was taken as an enzymatic solution.

(b) Cofactor solution

| | |
|---|---|
| B-nicotinamide adenine dinucleotide phosphate; reduced form (NADPH) | 3 mg |
| $MgCl_2$ solution (508 mg/10 ml) | 0.1 ml |
| 1.15% w/v KCl solution | 0.3 ml |
| 0.2 M phosphate buffer solution (pH 7.4) | 0.6 ml |

The above substances were mixed to a total volume of 1 ml to make the cofactor solution.

(c) Reaction solution

80 μl of the above enzymatic solution, 20 μl of the above cofactor solution and 2 μl of a methanol solution of ML-236B were mixed to make a final concentration of ML-236B of 1 mM. The resulting solution was shaken for 30 minutes at 37° C. M-4 was formed in the reaction mixture and identified by TLC (the same conditions as in Example 19).

EXAMPLE 21

(Preparation of M-4 sodium salt 2 mg of M-4 methyl ester were dissolved in 1 ml of a 0.1 N aqueous solution of sodium chloride and subjected to hydrolyzation at 30° C. for 1 hour. The reaction mixture was washed with 1 ml of chloroform and the resulting aqueous phase was adjusted to pH 8 with 0.1 N hydrochloric acid and passed through a XAD-2 column (about 5 ml). The column was washed with 20 ml of distilled water and the desired product was eluted with 15 ml of 50% v/v aqueous acetone. The acetone was distilled off from the eluate. The residue was confirmed by high-performance liquid chromatography to give a single peak (retention time was 13 minutes, eluted with 40% v/v aqueous methanol at 1 ml/minute). The residue was then lyophilized to give 0.8 mg of M-4 Na salt having the same properties as the product of Example 14.

EXAMPLE 22

Preparation of M-4 methyl ester

Each of twenty 500 ml. Evleumeyev flasks containing 100 ml. of a medium having the composition listed below was inoculated with spores of *Mucor hiemalis f. hiemalis* IFO-5834. The inoculum was subjected to shaking culture at 26° C. and 220 rpm. After 4 days, ML-236B was added to a final concentration of 0.05% w/v, and cultivation was conducted at 26° C. and 220 rpm for additional 6 days. The composition of the medium was (percentages are w/v):

| Glucose | 1.0% |
|---|---|
| Peptone | 0.2% |
| Meat extract | 0.1% |
| Yeast extract | 0.1% |
| Corn steep liquor | 0.3% |
| Tap water | balance |
| | (pH unadjusted). |

After completion of the cultivation, the filtrate was adjusted to a pH of 3 with trifluoroacetic acid. The mixture was then extracted three times, each time with 100 ml. of ethyl acetate. There was obtained a fraction containing M-4. M-4 has an Rf value of 0.45 on thin layer chromatography (Plate: Merck Silica gel Art 5715; Solvent: a 50:50:3 by volume mixture of benzene, acetone and acetic acid). The conversion ratio was 90%. This extract was washed with a saturated aqueous solution of sodium chloride, after which there was added an ethereal solution of diazomethane. The resulting mixture was allowed to stand for 30 minutes and then concentrated under reduced pressure to dryness. The residue was placed on a Lobar column (Merck Si 60, size A) and purified with a 1:1 by volume mixture of benzene and ethyl acetate. There were obtained about 600 mg. of M-4 methyl ester, having the same properties as the product of Example 13.

EXAMPLE 23

Preparation of M-4 lactone

The procedure described in Example 22 was repeated up to and including washing of the three ethyl acetate extracts with a saturated aqueous solution of sodium chloride. The resulting solution was then evaporated to dryness to give a lactone product. The product was recrystallized from ethyl acetate to give about 560 mg. (56%) of M-4 lactone, having the same properties as the product of Example 1.

EXAMPLE 24

Preparation of M-4 sodium salt

The procedure described in Example 22 was repeated to give 1.9 liters of the filtrate from the conversion reaction. This was extracted three times, each time with 1 liter of ethyl acetate to give fractions containing M-4. By immediately transferring these into a 5% w/v aqueous solution of sodium bicarbonate, there was obtained a fraction containing M-4 sodium salt. Then the M-4 sodium fraction was adjusted with 2 N hydrochloric acid to a pH of 7.0 and adsorbed on an HP-20 column (manufactured by Mitsubishi Chemical Industries). Washing with water and elution with 50% v/v aqueous acetone gave a fraction containing M-4 sodium salt, from which there were obtained 570 mg. (52%) of a freeze-dried product, having the properties described in Example 14.

EXAMPLE 25

Preparation of M-4

The procedure described in Example 22 was repeated, except that the following microorganisms were employed and the conversion to M-4 was as shown by the associated codes:

| Microorganism: | Conversion to M-4 |
|---|---|
| *Mucor hiemalis f. hiemalis* IFO-5303 | +4 |
| *Mucor hiemalis f. hiemalis* IFO-8567 | +4 |
| *Mucor hiemalis f. hiemalis* IFO-8449 | +4 |
| *Mucor hiemalis f. hiemalis* IFO-8448 | +4 |
| *Mucor hiemalis f. hiemalis* IFO-8565 | +4 |
| *Mucor hiemalis f. hiemalis* CBS-117.08 | +4 |
| *Mucor hiemalis f. hiemalis* CBS 109.19 | +4 |
| *Mucor hiemalis f. hiemalis* CBS-200.28 | +4 |
| *Mucor hiemalis f. hiemalis* CBS-242.35 | +4 |
| *Mucor hiemalis f. hiemalis* CBS-110.19 | +4 |
| *Mucor hiemalis f. hiemalis* CBS-201.65 | +4 |
| *Mucor bacilliformis* NRRL-2346 | trace |
| *Mucor circinelloides f. circinelloides* IFO-4554 | +1 |
| *Mucor circinelloides f. circinelloides* IFO-5775 | +1 |
| *Mucor hiemalis f. corticolus* NRRL-12473 | trace |
| *Mucor dimorphosporus* IFO-4556 | trace |
| *Mucor fragilis* CBS-236.35 | +1 |
| *Mucor genevensis* IFO-4585 | +1 |
| *Mucor globosus* NRRL-12474 | trace |
| *Mucor circinelloides f. griseo-cyanus* IFO-4563 | +1 |
| *Mucor heterosporus* NRRL-3154 | trace |
| *Mucor spinescens* IAM-6071 | trace |
| *Mucor chinensis* IFO-4772 | trace |
| *Rhizopus circinans* ATCC-1225 | +1 |
| *Rhizopus arrhizus* ATCC-11145 | +1 |
| *Zygorynchus moelleri* IFO-4833 | +1 |
| *Circinella muscae* IFO-4457 | +1 |
| *Circinell rigida* NRRL-2341 | trace |
| *Circinella umbellata* NRRL-1713 | +1 |
| *Circinella umbellata* IFO-4452 | +1 |
| *Circinella umbellata* IFO-5842 | +1 |
| *Actinomucor elegans* ATCC-6476 | +1 |
| *Phycomyces blakesleeanus* NRRL-12475 | trace |
| *Martierella isabellina* IFO-6739 | trace . |
| *Gongronella butlri* IFO-8080 | +1 |
| *Pycnoporus coccineus* NRRL-12476 | +3 |
| *Rhizoctonia solani* NRRL-12477 | +2 |

The codes representing the conversions to M-4 have the following meanings:

| trace | = | 0.5% or less |
|---|---|---|
| +1 | = | 0.5–5% |
| +2 | = | 5.0–10.0% |
| +3 | = | 10.0–30.0% |
| +4 | = | 70.0–90.0%. |

EXAMPLE 26

Preparation of IsoM-4' lactone

Each of twenty 500 ml. Sakaguchi flasks containing 100 ml. of a medium of the composition described in Example 22 was inoculated with spores of *Circinella muscae* IFO-4457. The inoculum was subjected to shaking culture at 26° C. and 120 spm. After 4 days, ML-236B was added to a final concentration of 0.05% w/v, and cultivation was conducted at 26° C. and 120 spm for a further 6 days.

After completion of the cultivation, the conversion reaction mixture was filtered, and the filtrate was adjusted with trifluoroacetic acid to a pH of 3.0. The mixture was then extracted three times, each time with 1 liter of ethyl acetate, giving a fraction containing IsoM-4'. This extract was washed with a saturated aqueous solution of sodium chloride and then evaporated to dryness. There was obtained a lactone product. The residue was placed on a Lobar column (Merck Si 60, size A) and purified with an ethyl acetate system, giving 12 mg. of IsoM-4' lactone, having the properties described in Example 7.

EXAMPLE 27

Preparation of M-4' lactone

Each of twenty 500 ml. Erlenmeyer flasks containing 100 ml. of a medium having the composition shown below was inoculated with spores of *Syncephalastrum nigrigans* NPRL-12478. The inoculum was subjected to shaking culture at 26° C. and 220 rpm. After 3 days, ML-236B was added to a final concentration of 0.05% w/v and cultivation was carried out at 26° C. and 220 rpm.

The composition of the medium was as follows (percentages are w/v):

| | |
|---|---|
| Glucose | 1% |
| Peptone | 0.2% |
| Meat extract | 0.1% |
| Yeast extract | 0.1% |
| Corn steep liquor | 0.3% |
| | (pH unadjusted). |

After completion of the cultivation, the conversion reaction mixture was filtered, and the filtrate was adjusted with trifluoroacetic acid to a pH of 3. The mixture was then extracted three times, each time with 1 liter of ethyl acetate to give a fraction containing M-4', which has an Rf value of 0.46 on thin layer chromatography (Plate: Merck silica gel Art 5715; solvent: a 50:50:3 by volume mixture of benzene, acetone and acetic acid). This extract was washed with a saturated aqueous solution of sodium chloride, dried over anhydrous sodium sulphate and subjected to lactonization by adding a catalytic amount of trifluoroacetic acid. The resulting mixture was then washed with a 5% w/v aqueous solution of sodium bicarbonate, dehydrated with anhydrous sodium sulphate and evaporated to dryness. The residue was crystallized from ethyl acetate to give about 180 mg. of M-4' lactone having the following physical properties:

(1) Nuclear Magnetic Resonance Spectrum:
  Measured in deuterochloroform at 100 MHz, using tetramethylsilane as the internal standard.
  δ ppm:
   6.01 (1H, doublet);
   5.90 (1H, quartet);
   5.75 (1H, multiplet);
   5.50 (1H, multiplet);
   4.60 (1H, multiplet);
   4.25 (1H, multiplet).

(2) Ultraviolet Absorption Spectrum (methanol) $\lambda_{max}$ nm: 230, 237, 245.

(3) Infrared Absorption Spectrum (KBr) $\nu$ cm$^{-1}$: 3500, 1720.

(4) Mass spectrum: M/e: 406(M+), 304, 286.

(5) Optical rotation: $[\alpha]_D^{25} = +310.9°$ (c=0.66, methanol).

(6) Melting point:
  141°–143° C.

(7) Elemental analysis:
  Calculated: C, 67.95%; H, 8.43%;
  Found: C, 68.05%; H, 8.37%.

(8) Thin Layer Chromatography:
  TLC plate: Merck silica gel Art 5715.
  Solvent: Benzene-acetone (1:1 by volume)
  Rf value 0.64.

EXAMPLE 28

Preparation of M-4' sodium salt

Following substantially the same cultivation procedures as in Example 27, there was obtained a conversion reaction mixture.

After completion of the cultivation, the conversion reaction mixture was filtered, and the filtrate was adjusted with trifluoroacetic acid to a pH of 3. It was then extracted three times, each time with 1 liter of ethyl acetate to give a fraction containing M-4', which was washed with a saturated aqueous solution of sodium chloride and immediately thereafter passed into a 5% w/v aqueous solution of sodium bicarbonate, to give a fraction containing M-4' sodium salt. The aqueous layer thus obtained was adjusted to pH 8.0 with 0.1 N hydrochloric acid and adsorbed on a Diaion HP 20 resin column (manufactured by Mitsubishi Chemical Industries). It was then eluted with 50% v/v aqueous acetone. The acetone was distilled off, and the residue was freeze-dried to give 1.41 g. of M-4' sodium salt, having the following physical properties:

(1) Nuclear Magnetic Resonance Spectrum:
  Measured in deuterochloroform at 60 MHz, using tetramethylsilane as the internal standard.
  δ ppm:
   6.00 (1H, doublet);
   5.95 (1H, quartet);
   5.70 (1H, broad singlet);
   5.50 (1H, broad singlet).

(2) Ultraviolet Absorption Spectrum (methanol) $\lambda_{max}$ nm: 230, 238, 246.

(3) Infrared Absorption Spectrum (KBr) $\nu$ cm$^{-1}$: 3400, 2900, 1680.

EXAMPLE 29

Preparation of M-4' methyl ester

Following substantially the same cultivation procedures as in Example 27, there was obtained a conversion reaction mixture.

After completion of the cultivation, the conversion mixture was filtered and the filtrate was adjusted with trifluoroacetic acid to a pH of 3. It was then extracted three times, each time with 1 liter of ethyl acetate. The combined extracts were washed with a saturated aqueous solution of sodium chloride and then an ethereal solution of diazomethane was added thereto. The resulting mixture was allowed to stand for 30 minutes and then concentrated under reduced pressure to dryness. The residue was purified using a Lober column (Merck RP-8, size A) and a 1:1 by volume mixture of benzene and acetone as the developing solvent. There were obtained 150 mg. of M-4' methyl ester as a colourless oily substance, having the following properties:

(1) Nuclear Magnetic Resonance Spectrum:

Measured in deuterochloroform at 60 MHz, using tetramethylsilane as the internal standard.

δ ppm:
6.01 (1H, doublet);
5.90 (1H, quartet);
5.75 (1H, broad singlet);
5.50 (1H, broad singlet);
3.70 (3H, singlet).

(2) Ultraviolet Absorption Spectrum (methanol) $\lambda_{max}$nm: 230, 238, 246.

(3) Infrared Absorption Spectrum (liquid film) $\nu$cm$^{-1}$: 3400, 1730.

(4) Mass analysis:

Measurement was made after alkylation with N,O-bis(trimethylsilyl)trifluoroacetamide using a mass spectrometer, type D-300 manufactured by Nippon Electronics.

M/e: 654 (M+).

We claim:

1. A process for preparing a compound of the formula (I).

wherein R represents a group of formula or or a ring-closed lactone, salt or ester thereof which comprises enzymatically hydroxylating a substrate selected from ML-236B having the formula or ML-236B carboxylic acid having the formula or a salt or ester of said ML-236B carboxylic acid with a microorganism of the genera Mucor, Rhizopus, Zygorynchus, Circinella, Actinomucor, Gongronella, Phycomyces, Martierella, Pycnoporus, Rhizoctonia, Absidia, Cunninghamella, Syncephalastrum and Streptomyces or with a cell-free, enzyme containing extract from said microorganisms to produce said compound of the formula (I), and recovering said compound of the formula (I).

2. A process as claimed in claim 1, wherein said microorganism is selected from the group consisting of:
Absidia coerulea
Cunninghamella echinulata
Syncephalastrum racemosum
Streptomyces roseochromogenus
Mucor hiemalis f. hiemalis
Mucor bacilliformis
Mucor circinellodes f. circinelloides
Mucor hiemalis f. corticolus
Mucor dinorphosporus
Mucor fragilis
Mucor genevensis
Mucor globosus
Mucor circinelloides f. griseo-cyanus
Mucor heterosporus
Mucor spinescens
Rhizopus chinensis
Rhizopus circinans
Rhizopus arrhizus
Zygorynchus moelleri
Circinella muscae
Circinella rigida
Circinella umbellata
Actinomucor, elegans
Phycomyces blakesleeanus
Martierella isbellina
Gongronella butleri
Pycnoporus coccineus
Rhizoctonia solani

*Syncephalastrum nigricans*
*Absidia glauca* var. *paradoxa*

3. A process as claimed in claim 2, wherein said microorganism is selected from the group consisting of:
*Absidia coerulea* IFO-4423
*Cunninghamella echinulata* IFO-4445
*Cunninghamella echinulata* IFO-4444
*Cunninghamella echinulata* ATCC-9244
*Syncephalastrum racemosum* IFO-4814
*Syncephalastrum racemosum* IFO-4828
*Streptomyces roseochromogenus* NRRL-1233
*Streptomyces roseochromogenus* IFO-3363
*Streptomyces roseochromogenus* IFO-3411
*Mucor hiemalis f. hiemalis* IFO-5834
*Mucor hiemalis f. hiemalis* IFO-5303
*Mucor hiemalis f. hiemalis* IFO-8567
*Mucor hiemalis f. hiemalis* IFO-8449
*Mucor hiemalis f. hiemalis* IFO-8448
*Mucor hiemalis f. hiemalis* IFO-8565
*Mucor hiemalis f. hiemalis* CBS-117.08
*Mucor hiemalis f. hiemalis* CBS-109.19
*Mucor hiemalis f. hiemalis* CBS-200.28
*Mucor hiemalis f. hiemalis* CBS-242.35
*Mucor hiemalis f. hiemalis* CBS-110.19
*Mucor hiemalis f. hiemalis* CBS-201.65
*Mucor bacilliformis* NRRL-2346
*Mucor circinelloides f. circinelloides* IFO-4554
*Mucor circinelloides f. circinelloides* IFO-5775
*Mucor hiemalis f. corticolus* NRRL-12473
*Mucor dimorphosporus* IFO-4556
*Mucor fragilis* CBS-236.35
*Mucor genevensis* IFO-4585
*Mucor globosus* NRRL-12474
*Mucor circinelloides f. griseo-cyanus* IFO-4563
*Mucor heterosporus* NRRL-3154
*Mucor spinescens* IAM-6071
*Rhizopus chinensis* IFO-4772
*Rhizopus circinans* ATCC-1225
*Rhizopus arrhizus* ATCC-11145
*Zygorynchus moelleri* IFO-4833
*Circinella muscae* IFO-4457
*Circinella rigida* NRRL-2341
*Circinella umbellata* NRRL-1713
*Circinella umbellata* IFO-4452
*Circinella umbellata* IFO-5842
*Phycomyces blakesleeanus* NRRL-12475
*Martierella isabellina* IFO-6739
*Gongronella butleri* IFO-8080
*Pycnoporus coccineus* NRRL-12476
*Rhizoctonia solani* NRRL-12477
*Syncephalastrum nigricans* NRRL-12478
*Syncephalastrum nigricans* NRRL-12479
*Syncephalastrum nigricans* NRRL-12480
*Absidia glauca* var. *paradoxa* IFO-4431
*Actinomucor elegans* ATCC-6476

4. A process as claimed in claim 3, wherein there is separated from the reaction mixture a compound selected from the group consisting of M-4, M-4', IsoM-4', a salt, ester or lactone of M-4, M-4' IsoM-4 or IsoM-4' or a mixture thereof.

5. A process as claimed in claim 4, wherein said ester is a $C_1$-$C_5$ alkyl ester.

6. A process as claimed in claim 4, wherein said ester is the methyl ester.

7. A process as claimed in claim 4, wherein said salt is an alkali metal salt.

8. A process as claimed in claim 4, wherein said salt is a sodium salt.

9. A process as claimed in claim 1, wherein said microorganism is selected from the group consisting of:
*Absidia coerulea*
*Cunninghamella echinulata*
*Syncephalastrum racemosum*
*Mucor hiemalis f. hiemalis*
*Mucor bacilliformis*
*Mucor circinellodies f. circinelloides*
*Mucor hiemalis f. corticolus*
*Mucor dimorphosporus*
*Mucor fragilis*
*Mucor genevensis*
*Mucor globosus*
*Mucor circinellodies f. griseo-cyanus*
*Mucor heterosporus*
*Mucor spinescens*
*Pycnoporus coccineus*
*Rhizoctonia solani*
*Syncephalastrum nigricans*

10. A process as claimed in claim 1, wherein said microorganism is selected from the group consisting of:
*Absidia coerulea* IFO-4423
*Cunninghamella echinulata* IFO-4445
*Cunninghamella echinulata* IFO-4444
*Cunninghamella echinulata* ATCC-9244
*Syncephalastrum racemosum* IFO-4814
*Syncephalastrum racemosum* IFO-4828
*Mucor hiemalis f. hiemalis* IFO-5834
*Mucor hiemalis f. hiemalis* IFO-5303
*Mucor hiemalis f. hiemalis* IFO-8567
*Mucor hiemalis f. hiemalis* IFO-8449
*Mucor hiemalis f. hiemalis* IFO-8448
*Mucor hiemalis f. hiemalis* IFO-8565
*Mucor hiemalis f. hiemalis* CBS-117.08
*Mucor hiemalis f. hiemalis* CBS-109.19
*Mucor hiemalis f. hiemalis* CBS-200.28
*Mucor hiemalis f. hiemalis* CBS-242.35
*Mucor hiemalis f. hiemalis* CBS-110.19
*Mucor hiemalis f. hiemalis* CBS-201.65
*Mucor bacilliformis* NRRL-2346
*Mucor circinelloides f. circinelloides* IFO-4554
*Mucor circinelloides f. circinelloides* IFO-5775
*Mucor hiemalis f. corticolus* NRRL-12473
*Mucor dimorphosporus* IFO-4556
*Mucor fragilis* CBS-236.35
*Mucor genevensis* IFO-4585
*Mucor globosus* NRRL-12474
*Mucor circinelloides f. griseo-cyanus* IFO-4563
*Mucor heterosporus* NRRL-3154
*Mucor spinescens* IAM-6071
*Pycnoporus coccineus* NRRL-12476
*Rhizoctonia solani* NRRL-12477
*Syncephalastrum nigricans* NRRL-12478
*Syncephalastrum nigricans* NRRL-12479 and
*Syncephalastrum nigricans* NRRL-12480.

11. A process as claimed in claim 1, wherein said microorganism is selected from the group consisting of:
*Mucor hiemalis f. hiemalis*
*Mucor circinelloides. f. circinelloides*
*Mucor fragilis*
*Mucor genevensis*
*Mucor circinelloides f. griseo-cyanus*
*Pycnoporus coccineus* and
*Rhizoctonia solani*.

12. The process of claim 1, wherein said microorganism is cultivated in a culture medium and said ML-236B or said ML-236B carboxylic acid or salt or ester thereof is added to said culture medium to produce said compound of the formula (I).

13. A process is for preparing a compound having the formula (a):

(wherein $R^1$ represents a hydrogen atom or a $C_1$-$C_5$ alkyl group), pharmaceutically acceptable salts of the acid wherein $R^1$ represents a hydrogen atom, and compounds of formula (b):

by enzymatically hydroxylating a substrate selected from the group consisting of ML236B or ML236B carboxylic acid with a microorganism selected from the group consisting of Syncephalastrum nigricans and Syncephalastrum racemosum and recovering said compounds.

14. A process as claimed in claim 13, wherein $R^1$ represents a hydrogen atom.

15. A process as claimed in claim 13, wherein $R^1$ represents a $C_1$-$C_5$ alkyl group.

16. A process as claimed in claim 13, wherein $R^1$ represents a methyl group.

17. A process as claimed in claim 13, wherein said salt is an alkali metal salt.

18. A process as claimed in claim 17, wherein said salt is a sodium salt.

19. A process for preparing a compound having the formula (c):

(wherein $R^1$ represents a hydrogen atom or a $C_1$-$C_5$ alkyl group), pharmaceutically acceptable salts of the acid wherein $R^1$ represents a hydrogen atom, and compounds of formula (d):

by enzymatically hydroxylating a substrate selected from the group consisting of ML236B or ML236B carboxylic acid with a microorganism selected from the group consisting of Absidia coerulea and Cunninghamella echinulata and recovering said compounds.

20. A process as claimed in claim 19, wherein $R^1$ represents a hydrogen atom.

21. A process as claimed in claim 19, wherein $R^1$ represents a $C_1$-$C_5$ alkyl group.

22. A process as claimed in claim 19, wherein $R^1$ represents a methyl group.

23. A process as claimed in claim 19, wherein said salt is an alkali metal salt.

24. A process as claimed in claim 23, wherein said salt is a sodium salt.

* * * * *